(12) United States Patent
Pan et al.

(10) Patent No.: US 8,197,407 B2
(45) Date of Patent: Jun. 12, 2012

(54) METHOD AND APPARATUS FOR SUB-HARMONIC CONTRAST IMAGING

(75) Inventors: Lihong Pan, Brookfield, WI (US); Feng Lin, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 907 days.

(21) Appl. No.: 12/045,434

(22) Filed: Mar. 10, 2008

(65) Prior Publication Data

US 2009/0227872 A1    Sep. 10, 2009

(51) Int. Cl.
*A61B 8/00* (2006.01)

(52) U.S. Cl. .......... 600/437; 600/443; 600/458

(58) Field of Classification Search .......... 128/916; 235/472, 462; 600/407, 410, 437, 443, 447, 600/453, 458, 459; 73/625–627
See application file for complete search history.

(56) References Cited

U.S. PATENT DOCUMENTS

| | | | |
|---|---|---|---|
| 6,193,659 B1 * | 2/2001 | Ramamurthy et al. | 600/443 |
| 6,221,018 B1 * | 4/2001 | Ramamurthy et al. | 600/443 |
| 6,494,841 B1 | 12/2002 | Thomas et al. | |
| 6,602,195 B1 | 8/2003 | Krishnan et al. | |
| 6,682,482 B1 * | 1/2004 | Krishnan | 600/437 |
| 2003/0100833 A1 * | 5/2003 | He et al. | 600/446 |
| 2004/0030251 A1 * | 2/2004 | Ebbini et al. | 600/443 |
| 2005/0004469 A1 * | 1/2005 | Tsuzuki | 600/458 |

* cited by examiner

*Primary Examiner* — Brian Casler
*Assistant Examiner* — Michael N Fisher
(74) *Attorney, Agent, or Firm* — The Small Patent Law Group; Dean D. Small

(57) ABSTRACT

A non-linear response may be measured by transmitting a first pulse at an amplitude and transmit frequency, using an aperture having N elements. A first response is measured at a sub-harmonic frequency based on the transmit frequency. At least second and third pulses are transmitted at the amplitude and transmit frequency. At least second and third responses are measured at the sub-harmonic frequency. The second and third pulses have the same phase with respect to each other and use first and second sub-apertures that have different ones of the N elements. A sum of the elements within the first and second sub-apertures is equal to N. Alternatively, at least two pulses having the same aperture and different amplitudes may be transmitted, and the responses measured at the sub-harmonic frequency. The responses are combined to suppress linear echoes and determine a non-linear response.

22 Claims, 10 Drawing Sheets

METHOD AND APPARATUS FOR SUB-HARMONIC CONTRAST IMAGING

BACKGROUND OF THE INVENTION

This invention relates generally to diagnostic ultrasound medical imaging systems, and more particularly, to methods and apparatus for detecting nonlinear echoes from contrast agents.

Contrast agents (e.g. micro-bubbles) can be used in diagnostic medical imaging to aid in the detection/classification of diseased tissues. In some detection methods, the nonlinear response of the contrast agent relative to tissue is used to distinguish between ultrasound echoes resulting from the presence of contrast agent and echoes resulting from tissue. For example, contrast agents may be used to boost blood echo signals in blood vessels.

Pulse inversion harmonic contrast imaging is an ultrasound contrast imaging method where two pulses having the same amplitude and 180 degree phase shift are transmitted to the body. The signal is detected in the harmonic frequency, which is twice the transmit frequency. Another method is amplitude modulation contrast imaging where pulses with different amplitudes are transmitted to the body. The signal is detected in the fundamental frequency. Other methods of contrast imaging are desired to improve the image quality when using various contrast agents.

BRIEF DESCRIPTION OF THE INVENTION

In accordance with an embodiment of the present invention, an imaging apparatus that comprises at least a transmitter and a transducer comprising at least N elements that are excitable by the transmitter may be used in a method for measuring a non-linear response. The method comprises transmitting a first pulse from the transducer at an amplitude and transmit frequency and using an aperture that comprises N elements. A first response thereto is measured at a sub-harmonic frequency that is based on the transmit frequency. At least second and third pulses are transmitted from the transducer at the amplitude and the transmit frequency. At least second and third responses thereto are measured at the sub-harmonic frequency. The second and third pulses have the same phase with respect to each other and use first and second sub-apertures that comprise different ones of the N elements, and a sum of the elements within the first and second sub-apertures is equal to N. The first, second and third responses are combined to suppress linear echoes and determine a non-linear response. A representation of the non-linear response is then displayed on a display.

In another embodiment, a diagnostic imaging apparatus for measuring a non-linear response comprises a transmitter and a transducer having at least N elements excitable by the transmitter. A receiver receives echo return signals from the elements. A combining module determines a non-linear response based on signals received from the elements, and a display displays a representation of the determined non-linear response. The apparatus is configured to transmit a first pulse from the transducer at an amplitude and a transmit frequency, and to measure a first response thereto. The first pulse uses an aperture that comprises the N elements. The apparatus transmits at least second and third pulses from the transducer and measures at least second and third responses thereto. The at least second and third pulses have the amplitude and the transmit frequency. The at least second and third pulses use different sub-apertures that each comprise a portion of the N elements wherein the sub-apertures comprise a total of N elements. The first response and the at least second and third responses are combined to suppress linear echoes and determine a non-linear response. A sub-harmonic signal is measured based on the combined response and the transmit frequency, and a representation of the non-linear response based on the sub-harmonic signal is displayed on the display.

In yet another embodiment, a method for measuring a non-linear response using an ultrasound imaging apparatus comprises transmitting a first pulse from a transducer at a first transmit amplitude and a transmit frequency. A first response thereto is measured. A second pulse is transmitted from the transducer and has a reduced transmit amplitude with respect to the first transmit amplitude. A second response thereto is measured. The first and second pulses both use the N transducer elements. The first and second responses are combined to suppress linear echoes and determine a non-linear response. At least one sub-harmonic signal is measured based on the first and second responses and the transmit frequency, and a representation of the non-linear response is displayed on the display.

DETAILED DESCRIPTION OF THE INVENTION

Figure 1:
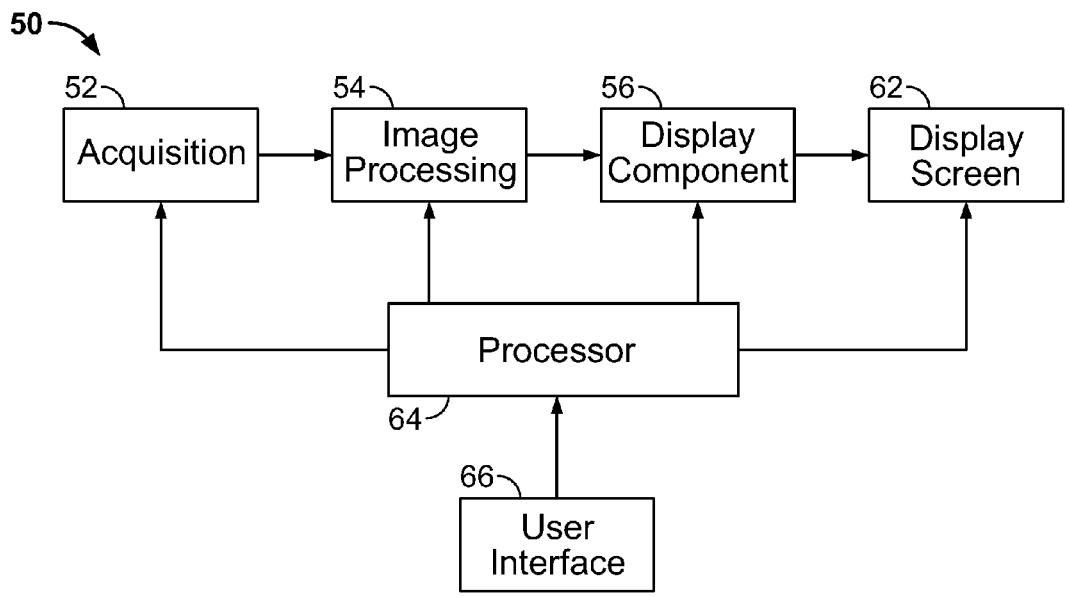
FIG. 1 is a block diagram of a diagnostic imaging apparatus constructed in accordance with an embodiment of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments of the invention provide a diagnostic imaging apparatus 50 as shown in FIG. 1. Diagnostic imaging apparatus 50 may be any type of system, for example, different types of medical imaging systems, such as an ultrasound imaging apparatus or a multi-modality imaging apparatus, among others, in which the phase of the transmitted signal is controlled and non-linearities with respect to the signal in an object of interest are significant. The various embodiment are not limited to medical imaging systems or imaging systems for imaging human subjects, but may include veterinary or non-medical systems for imaging non-human objects etc.

Diagnostic imaging apparatus 50 generally includes an acquisition component 52 configured to acquire image data (e.g., ultrasound image data). Acquisition component 52 may be, for example, a probe, scanner or other similar device for scanning an object or volume of interest. Acquisition component 52 is connected to an image processing component 54. Image processing component 54 is any type of image processor capable of processing the acquired image data and is connected to a display component 56. Display component 56 configures or formats the processed image data for display on a display 62. The display 62 may be any type of screen capable of displaying images, graphics, text, etc. For example, the display 62 may be a cathode ray tube (CRT) screen, a liquid crystal display (LCD) screen or a plasma screen, among others.

A processor 64 (e.g., computer) or other processing unit controls the various operations within diagnostic imaging apparatus 50. For example, processor 64 may receive user inputs from a user interface 66 and display requested image data or adjust the settings for the displayed image data.

Figure 2:
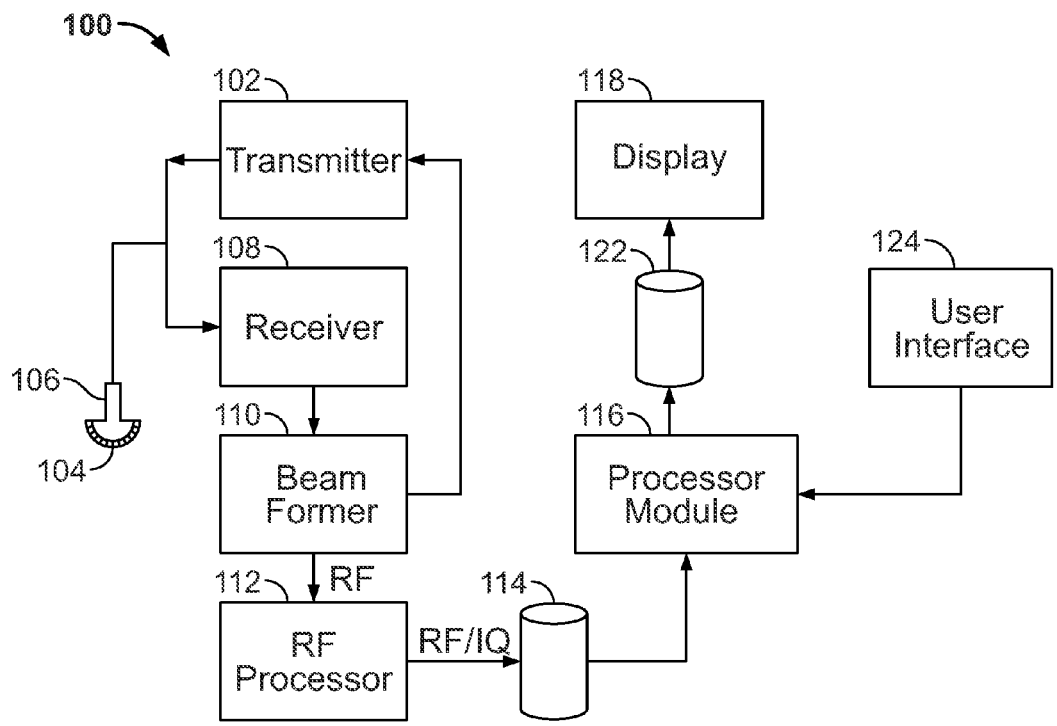
FIG. 2 is a block diagram of an ultrasound imaging apparatus constructed in accordance with an embodiment of the invention.

Diagnostic imaging apparatus 50 may be, for example, an ultrasound imaging apparatus 100 shown in FIG. 2. Ultrasound imaging apparatus 100 includes a transmitter 102 that drives an array of elements 104 (e.g., piezoelectric or other elements) within a transducer 106 to emit pulsed ultrasonic signals into a body. The transmit energy is focused at a given position through the control of a beamformer 110. Alternatively, plane wave ultrasound energy may be transmitted to the body without focus to a particular location. It should be noted that at a given focus depth, the elements 104 that are excited may be less than the total number of elements 104 forming the array. For example, if the total number of elements 104 is n, then at a given focus depth, the full aperture $N \leq n$. A variety of geometries may be used. The ultrasonic signals are back-scattered from structures in the body, like blood cells or muscular tissue, to produce echoes that return to the elements 104. The echoes are received by a receiver 108. The received echoes are passed through the beamformer 110, which performs beamforming and outputs an RF signal. The RF signal then passes through an RF processor 112. Alternatively, RF processor 112 may include a complex demodulator (not shown) that demodulates the RF signal to form IQ data pairs representative of the echo signals. The RF or IQ signal data may then be routed directly to a memory 114 for storage.

Ultrasound imaging apparatus 100 also includes a processor module 116 to process the acquired ultrasound information (e.g., RF signal data or IQ data pairs) and prepare frames of ultrasound information for display on display 118. Processor module 116 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 114 during a scanning session and then processed and displayed in off-line operation.

Processor module 116 is connected to a user interface 124 that may control operation of processor module 116. Display 118 includes one or more monitors that present patient information, including diagnostic ultrasound images to the user for diagnosis and analysis. One or both of memory 114 and memory 122 may store three-dimensional data sets of the ultrasound data, where such 3-D data sets are accessed to present two-dimensional (2D) and three-dimensional (3D) images. The images may be modified and the display settings of display 118 also manually adjusted using user interface 124.

Ultrasound imaging apparatus 100 may obtain volumetric data sets by various techniques (e.g., 3D scanning, real-time 3D imaging, volume scanning, 2D scanning with transducers having positioning sensors, freehand scanning using a Voxel correlation technique, 2D or matrix array transducers and the like). Transducer 106 is moved, such as along a linear or arcuate path, while scanning a region of interest (ROI). At each linear or arcuate position, transducer 106 obtains scan planes that are stored in memory 114.

Figure 3:
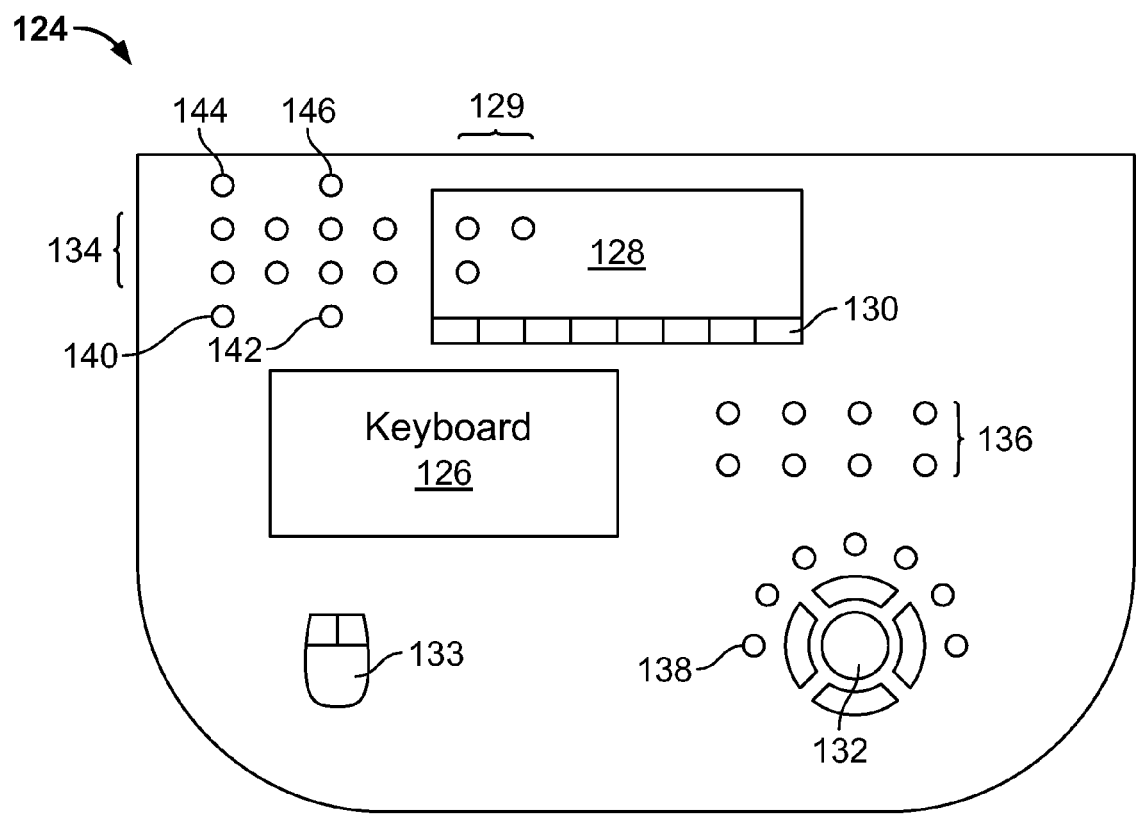
FIG. 3 is a top plan view of a user interface constructed in accordance with an embodiment of the invention.

FIG. 3 illustrates user interface 124 constructed in accordance with one embodiment of the invention. User interface 124 can include a keyboard 126, a mouse 133 (more commonly found in off-line imaging systems and workstations than in an ultrasound imaging apparatus), a touch screen 128, a series of soft keys 130 proximate the touch screen 128, a trackball 132, view position buttons 134, mode buttons 136 and control or operation keys 138. Soft keys 130 are assigned different functions on touch screen 128 depending upon a selected examination mode, stage of examination and the like. Trackball 132 and keys 138 are used to control the display of images on the display 118 and control various options, for example, zoom, rotate, viewing mode, examination mode, etc. For example, view position buttons 134 may change different views of the displayed image. Optionally, view position buttons 134 may be implemented as touch areas 129 on touch screen 128. As a further option, the size, position and orientation of the displayed image may be controlled partially or entirely by touch areas provided on touch screen 128 and/or by the soft keys 130.

User interface 124 also includes other controls, such as a save command/option 140 and a restore command/option 142 to save or restore certain image characteristics or changes to the displayed image. However, it should be noted that the various controls may be used to adjust or control different settings, display options, etc. For example, user interface 124 may include a brightness control button 144 that allows a user to manually adjust screen brightness and a contrast control button 146 that allows a user to manually adjust screen contrast.

Figure 4:
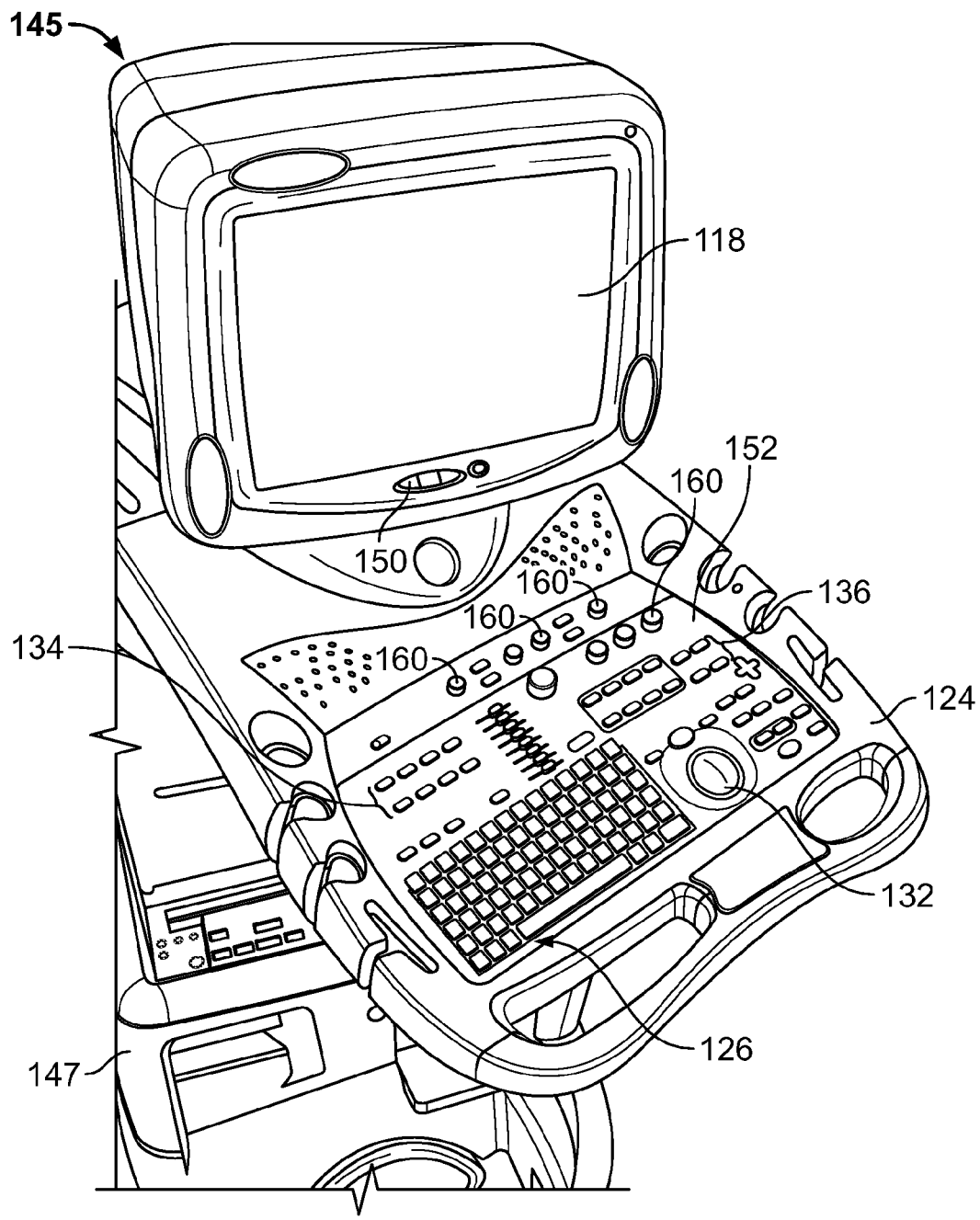
FIG. 4 is a perspective view of a portable medical imaging apparatus constructed in accordance with an embodiment of the invention.

Embodiments of the present invention may, for example, be implemented in a portable imaging apparatus 145 (e.g., portable ultrasound apparatus) provided on a movable base 147, as shown in FIG. 4. Manual screen adjustment controls 150 (e.g., brightness and contrast controls) are provided on display 118. It should be understood that display 118 may be separate or separable from user interface 124. User interface 124 may optionally be a touchscreen, allowing the user to select options by touching displayed graphics, icons, and the like.

User interface 124 of FIG. 4 also includes other optional control buttons 152 that may be used to control portable imaging apparatus 145 as desired or needed, and/or as typically provided. User interface 124 provides multiple interface options that the user may physically manipulate to interact with ultrasound data and other data that may be displayed, as well as to input information and set and change scanning parameters. The interface options may be used for specific inputs, programmable inputs, contextual inputs, and the like. Different types of physical controls are provided as different physical actions are more intuitive to the user for accomplishing specific system actions and thus achieving specific system responses.

For example, multi-function controls 160 are positioned proximate to display 118 and provide a plurality of different physical states. For example, a single multi-function control may provide movement functionality of a clockwise/counter-clockwise (CW/CCW) rotary, up/down toggle, left/right toggle, other positional toggle, and on/off or pushbutton, thus allowing a plurality of different states. Different combinations are possible and are not limited to those discussed herein. The multi-function controls 160 may be configured, for example, as joystick rotary controls.

Figure 5:
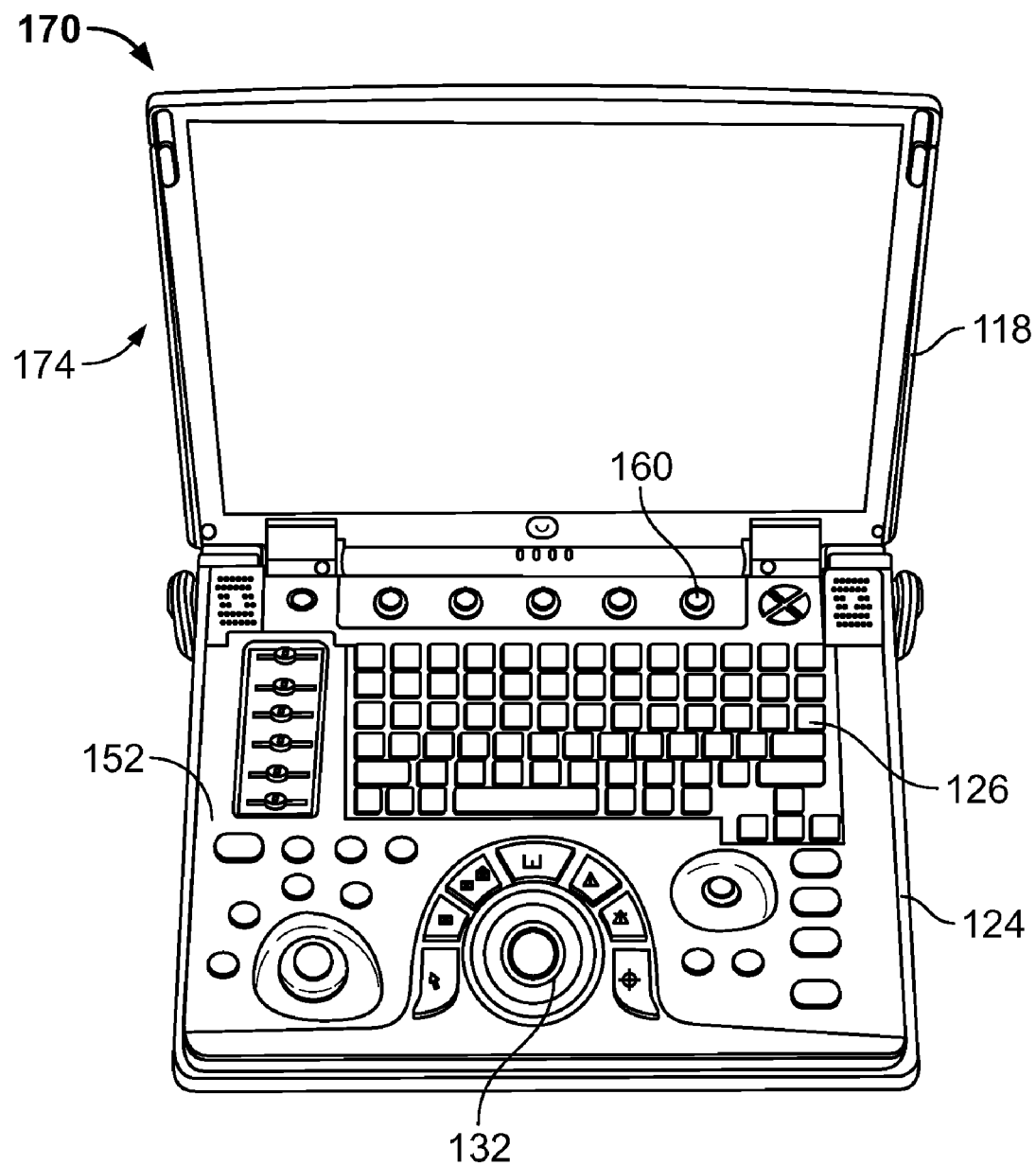
FIG. 5 is a perspective view of a hand carried medical imaging apparatus constructed in accordance with another embodiment of the invention.

Embodiments of the present invention may also be provided in connection with a hand carried imaging apparatus 170 as shown in FIG. 5, wherein display 118 and user interface 124 form a single unit. The hand carried imaging apparatus 170 may be, for example, a handheld or hand carried ultrasound imaging device, such as a miniaturized ultrasound apparatus. As used herein, "miniaturized" means that the ultrasound apparatus is configured to be carried in a person's hand, pocket, briefcase-sized case, or backpack. For example, the hand carried imaging apparatus 170 may be a hand carried device having a size of a typical laptop computer, for instance, having dimensions of approximately 2.5 inches in depth, approximately 14 inches in width, and approximately 12 inches in height. The hand carried imaging apparatus 170 may weigh about ten pounds.

Figure 6:
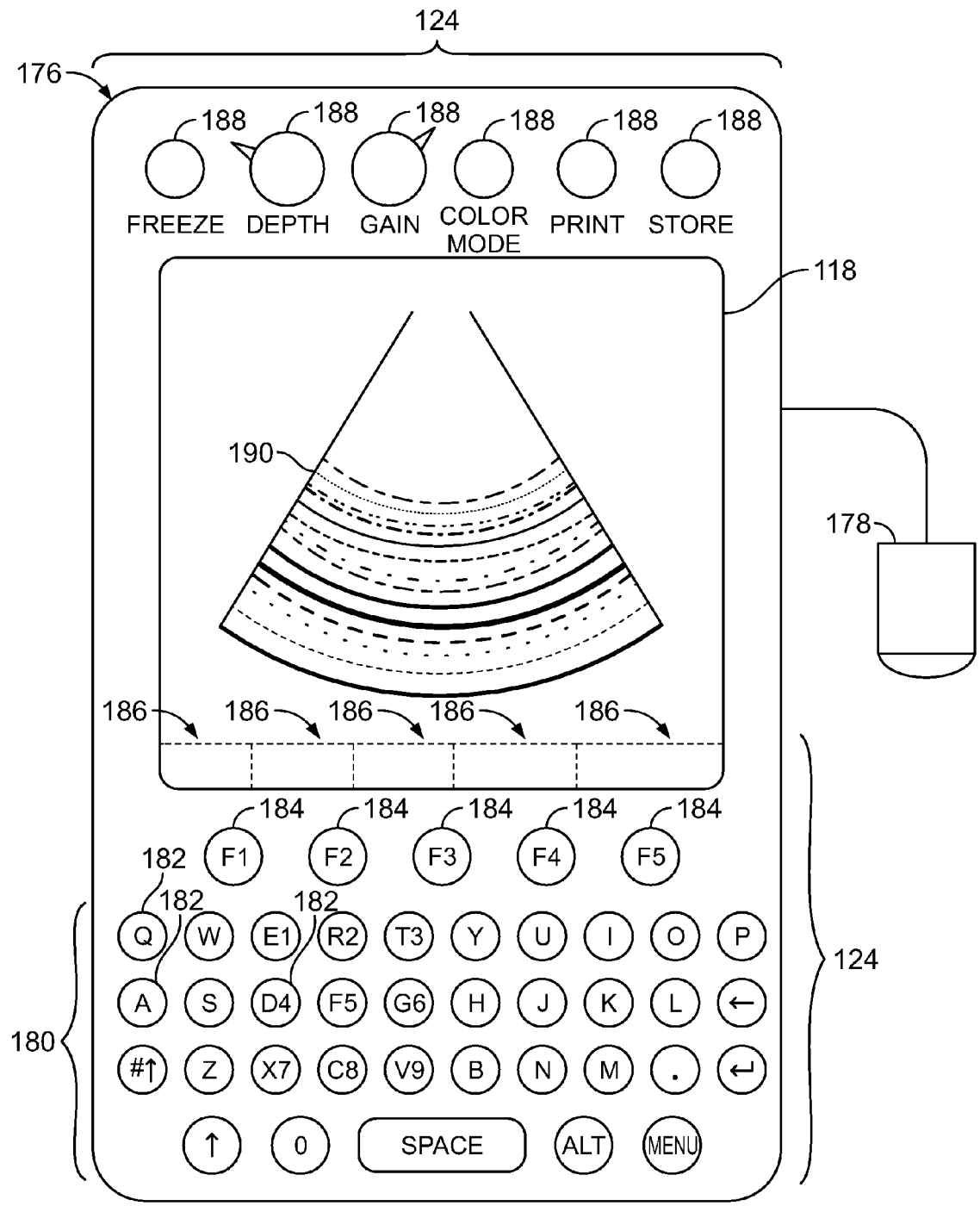
FIG. 6 is a perspective view of a pocket-sized medical imaging apparatus constructed in accordance with another embodiment of the invention.

Embodiments of the present invention may also be provided in connection with a pocket-sized imaging apparatus 176 as shown in FIG. 6, wherein display 118 and user interface 124 form a single hand held unit. By way of example, the pocket-sized imaging apparatus 176 may be a pocket-sized or hand-sized ultrasound apparatus approximately 2 inches wide, approximately 4 inches in length, and approximately 0.5 inches in depth and weigh less than 3 ounces. The pocket-sized imaging apparatus 176 generally includes display 118, user interface 124, which may include a keyboard and an input/output (I/O) port for connection to a scanning device, for example, an ultrasound probe 178. Display 118 may be, for example, a 320×320 pixel color LCD display (on which a medical image 190 may be displayed). A typewriter-like keyboard 180 of buttons 182 may be included in user interface 124. Multi-function controls 184 may each be assigned functions in accordance with the mode of system operation as previously discussed. Label display areas 186 associated with the multi-function controls 184 may be included as necessary on display 118. The device may also have additional keys and/or controls 188 for special purpose functions, which may include, but are not limited to "freeze," "depth control," "gain control," "color-mode," "print," and "store."

The various embodiments may be implemented in connection with miniaturized imaging systems having different dimensions, weights, and power consumption. In some embodiments, the pocket-sized ultrasound apparatus may provide the same functionality as ultrasound imaging apparatus 100 (shown in FIG. 2).

In embodiments of the present invention, a sub-harmonic contrast imaging technique transmits multiple pulses (e.g. two or more pulses) to an object, for example, a body. In low mechanical index (MI) contrast imaging, the tissue signal response is linear or nearly linear as a function of amplitude while the response of the contrast agent is nonlinear. The receive signals of the multiple pulses may be detected at the sub-harmonic frequency, which is approximately half of the transmit frequency. Alternatively, the sub-harmonic signal may be measured after the received signals are combined. Depending upon the transmit signals used, the receive signals may be weighted such that for linear response the receive signals sum to zero. The tissue signal or linear echoes are thus cancelled out, leaving or preserving the contrast signal (e.g. nonlinear echo response) for viewing. For example, a particular contrast agent may have a stronger response at the sub-harmonic frequency compared to the response at the second harmonic frequency. Therefore, a stronger contrast signal may be detected at the sub-harmonic frequency.

Figure 7:
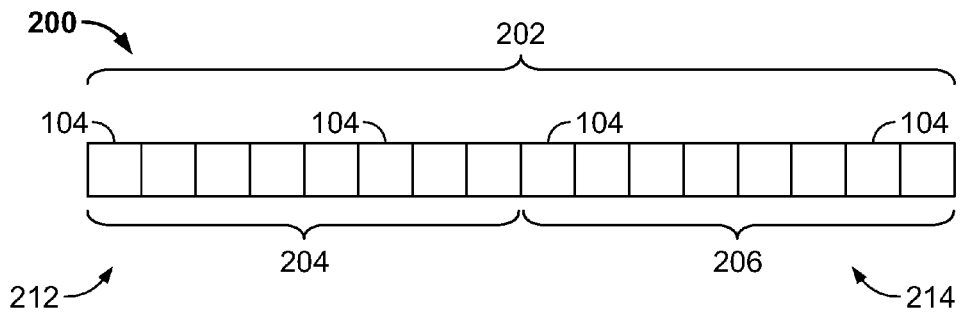
FIG. 7 is a drawing illustrating the selection of apertures and sub-apertures to form exemplary pulse sequences in one embodiment of the present invention.
Figure 8:
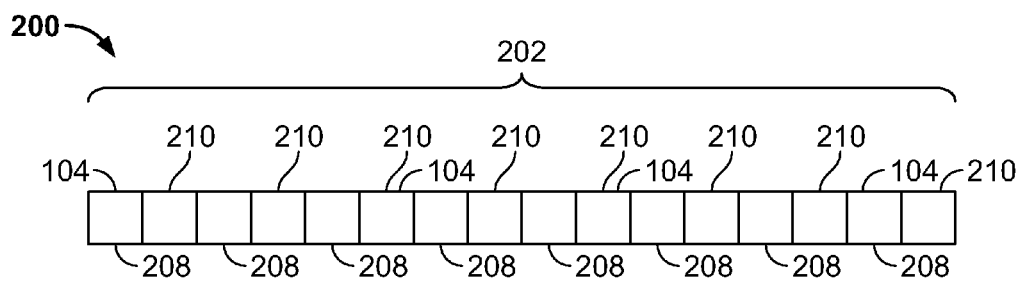
FIG. 8 is a drawing illustrating the selection of apertures and sub-apertures to form other exemplary pulse sequences in another embodiment of the present invention.

A number of different pulse sequences may be used to accomplish sub-harmonic contrast imaging. FIGS. 7 and 8 are drawings illustrating the selection of apertures and sub-apertures to form different pulse sequences used in sub-harmonic imaging. In these exemplary pulse sequences, the number of elements 104 that are turned on for each pulse is varied to achieve a desired change in summed amplitude, while the same transmit amplitude is used for each pulse. In embodiments discussed further below, the transmit amplitude may be changed to accomplish the pulse amplitude modulation.

An array 200 of elements 104 of the transducer 106 (shown in FIG. 1) is shown. It should be understood that more elements 104 may be included and that the array 200 may also be a 2D array. Turning to FIG. 7, aperture 202 may have N elements 104 that are used to form a sequence of three pulses. The N elements 104 may represent all of the elements 104 within the transducer 106 or may be a portion of the elements 104, wherein the transducer 106 may be divided into more than one aperture 202 or certain elements 104 may not be used. First and second sub-apertures 204 and 206 may be complementary sub-apertures, meaning that the sum of the complementary sub-apertures equals the full aperture 202. For example, a sub-aperture can be selected by exciting with the transmitter 102 only those elements 104 that belong to the sub-aperture, or by physically blocking the transmissions of a signal from the elements 104 outside of the sub-aperture in embodiments in which it is feasible to do so.

In one embodiment, the first and second sub-apertures 204 and 206 may each comprise exactly half of the elements 104 of the entire array 200 of elements 104 of the transducer 106 on opposite sides 212 and 214 of the aperture 202. First sub-aperture 204 is thus located on one side 212 of aperture 202 and second sub-aperture 206 is located on the other side 214 of aperture 202.

Although the pulses below are referred to as first, second and third pulses, it should be noted that the pulses may be transmitted in any order. In one pulse sequence, a first pulse turns on all of the n elements 104, or turns on all of the elements 104 within the aperture 202. A second pulse turns on the first sub-aperture 204 that is one-half of the n elements 104, and a third pulse turns on the second sub-aperture 206 that is the other one-half of the n elements 104 that were not turned on in the second pulse.

In FIG. 8, first and second sub-apertures 208 and 210 may be formed from all odd or even elements 104, alternating or interleaved across the aperture 202. As shown, the first and second sub-apertures 208 and 210 comprise interleaved halves of the array 200 of elements 104 of the transducer 106. For example, the second pulse may turn on elements within sub-aperture 208 and the third pulse may turn on elements within sub-aperture 210. In other embodiments (not shown) the first and second sub-apertures 208 and 210 may each be formed of any periodic half selection, random half selection, pseudo-random half selection, or patterned half arrangement of one-half of the n elements 104. In still other embodiments (not shown) the first and second sub-apertures 204 and 206 may have unequal amounts of elements 104 as long as the number of elements 104 in the first sub-aperture 204 plus the number of elements 104 in the second sub-aperture 206 are equal to the total number of elements 104 in the aperture 202. In some cases, the received bubble signal strength may be strongest if each of the first and second sub-apertures 204 and 206 has one-half of the total number of elements 104.

Also, transmit sequences that have more than three pulses may also achieve good tissue cancellation. For example, one transmit pulse may use all of the elements 104 (e.g. aperture 202) and the other M transmit pulses each uses less than n elements as long as the sum of the elements 104 in all of the sub-apertures is the same as the full aperture. However, a greater number of pulses in the transmit sequence may result in a lower frame rate.

For each of the transmit pulses, the transmit amplitude on each element 104 is the same. Therefore, at the focal point or at a selected point within the body or object, the summed amplitude for the full aperture 202, wherein all elements 104 are turned on, is twice as high as that for each of the sub-apertures that have half the number of elements 104 turned on. Assuming that the transmit order is the first sub-aperture 204, the full aperture 202, and the second sub-aperture 206, the summed amplitude at the focal point is [0.5, 1, 0.5]. The phases of the pulses of the first and second sub-apertures 204 and 206 and the full aperture 202 are the same.

In another embodiment, the pulse phase of the aperture 202 may be anti-symmetric or 180 degrees shifted with respect to the first and second sub-apertures 204 and 206, which are the same as each other. If the full aperture pulse is in the 180 degree shift, the transmit sequence is represented as [0.5, −1, 0.5] wherein the number (e.g. 0.5 or 1) is the relative summed amplitude and the sign stands for the phase.

In low MI contrast imaging using sub-apertures that are the same size, the acoustic property of tissue is linear, and the tissue signal received from the full aperture 202 is two times as much as the tissue signal received from one of the sub-apertures. In contrast, because the signal response to the contrast agent is non-linear, the contrast signal from the full aperture 202 is not two times as much as the contrast signal response from one of the first and second sub-apertures 204 and 206.

In some cases, weighting may be used to cancel the fundamental or tissue signal. For the transmit sequence of [0.5, 1, 0.5], a weighting for receiving of [1, −1, 1] may be used. After weighting, the three signals may be summed, canceling the tissue signal (linear echo), while leaving the non-linear echo portion of the signal. Therefore, only the contrast bubble signal is left in the summed signal. For the transmit sequence of [0.5, −1, 0.5], a weighting for receiving of [1, 1, 1] may be used.

In another embodiment, amplitude change may also be achieved by adjusting a transmit voltage or current. For each transmit pulse, the same number of transducer elements 104 are turned on. In other words, the aperture used for each transmit pulse has the same number of elements 104. For example, for a two pulse transmit sequence, in the first pulse, the transmit pulse amplitude is A1. By adjusting the transmit voltage or current, the second pulse is set to 0.5*A1. If the first and second pulses are in the same phase, the transmit sequence is [1, 0.5]. To cancel out the tissue signal, the receive weighting is set to [1, −2]. In another two pulse transmit sequence, the two transmit pulse phases may be set at a 180 degree shift with respect to each other, giving a transmit sequence of [1, −0.5]. To cancel the tissue signal, the receive weighting is [1, 2]. In other words, if the transmit sequence is [t1, t2] and the receive weighting is [r1, r2], then t1*r1 +t2*r2=0.

Transmit sequences with more than two pulses may also be used as long as t1*r1+t2*r2+ . . . +tx*rx=0. As discussed above, higher numbers of transmit pulses reduce the image frame rate, which may be undesirable in some applications. Varying the transmit voltage or current may require that the pulse amplitudes at the two or more levels be linear with respect to each other in order to achieve good tissue cancellation. For example, if the transmitter 102 outputs an amplitude of t1 that is A, it is desirable that the amplitude of t2 is 0.5*A. If the amplitude of t2 is some level other than 0.5*A, an additional adjustment parameter may be applied either in the transmit voltage or current or in the receiving weighting so that t1*r1+t2*r2+ . . . +tx*rx=0.

Figure 9:
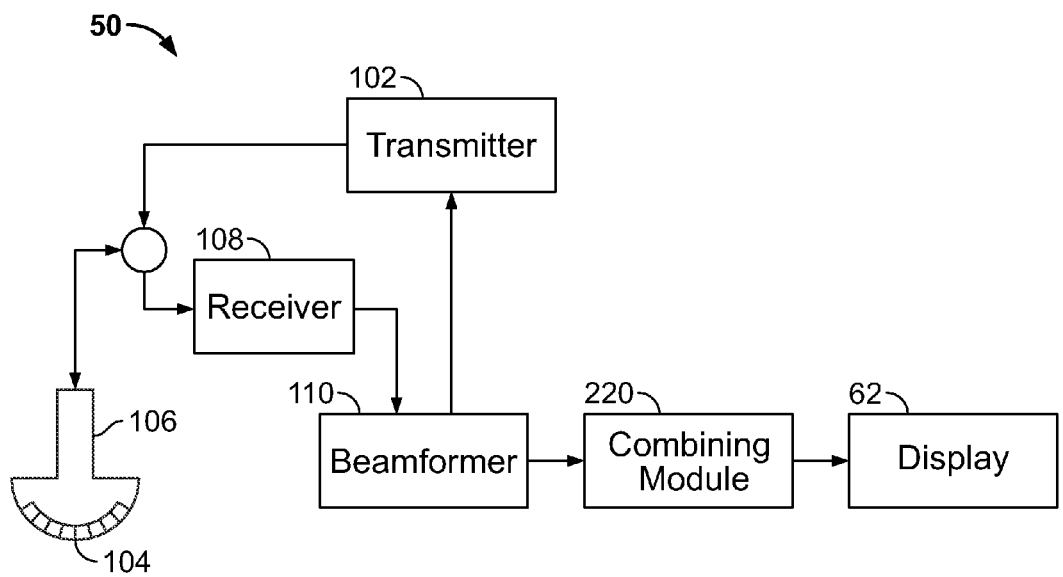
FIG. 9 is a schematic block diagram representative of some apparatus embodiments of the present invention.

A technical effect of at least one embodiment of the present invention is to measure and/or display a non-linear response, such as a response due to contrast agent, by receiving multiple transmit pulses at the sub-harmonic frequency. FIG. 9 is a schematic block diagram of an embodiment of the present invention configured to measure a non-linear response from a target (which may comprise a contrast agent). FIGS. 10-13 are flow charts of method embodiments that use an imaging apparatus 50 of the type shown in FIG. 9 to transmit multiple pulses and detect corresponding responses at the sub-harmonic frequency.

Referring to FIG. 9, imaging apparatus 50 includes a transmitter 102, a transducer 106 having a plurality n of excitable transducer elements 104 that are excitable by a transmitter 102, a receiver 108 and a beamformer 110. The receiver 108 is configured to detect echo return signals from transducer elements 104. The received signals may be detected at the sub-harmonic frequency. A combining module 220 is configured to determine a non-linear response based on multiple received signals. In some embodiments, the sub-harmonic signal may be measured based on the combined signal. A display 62 is configured to display a representation of the determined non-linear response.

Figure 10:
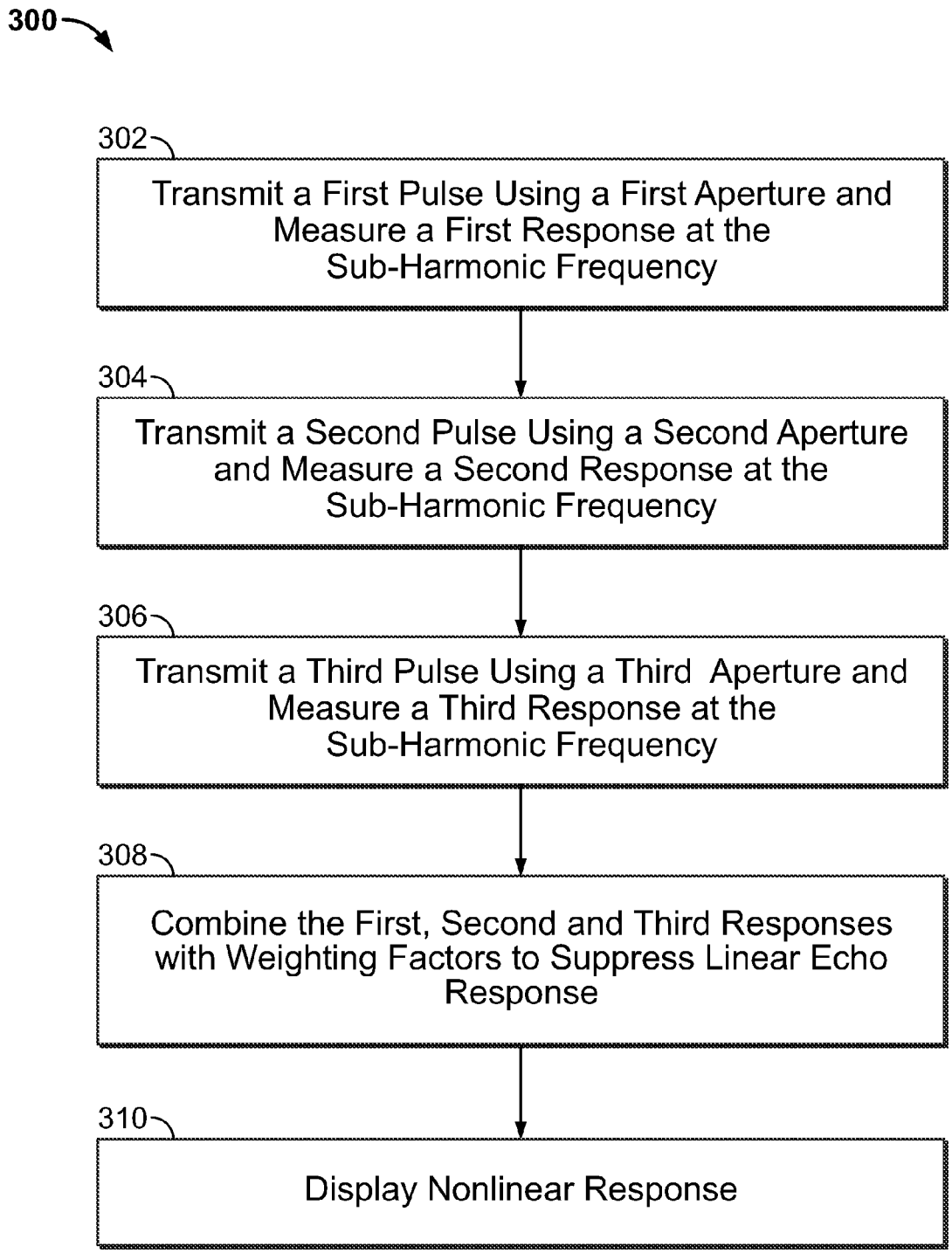
FIGS. 10 and 11 are flow charts of methods for measuring a non-linear response using full and sub-apertures in accordance with an embodiment of the invention.

FIG. 10 illustrates a method 300 for measuring a non-linear response by detecting the sub-harmonic signal based on multiple transmit pulses with full and sub-apertures. In all transmits, each activated element 104 transmits at the same amplitude. In other words, each element 104 is excited with the same level of current or voltage. Therefore, the summed pulse amplitude of the full aperture (e.g. as may be measured within the body or subject) is not the same as the summed pulse amplitude of a sub-aperture. At 302, the transmitter 102 transmits a first pulse at a transmit frequency from the transducer 106. A region of interest or focal point may be used, or the pulse may be unfocused. In one example, the first pulse may be transmitted using a portion of the aperture 202, such as the first sub-aperture 204 (of FIG. 7) or the sub-aperture 208 (of FIG. 8). The receiver 108 detects or measures a first response thereto as the sub-harmonic signal at a sub-harmonic frequency that is based on the transmit frequency. Alternatively, the first response may be filtered based on the sub-harmonic frequency to measure the sub-harmonic signal. For example, if the transmit frequency is 5 MHz, the sub-harmonic frequency may be approximately 2.5 MHz.

At 304, the transmitter 102 transmits a second pulse at the same transmit frequency as the first pulse from transducer 106 and measures a second response thereto as the sub-harmonic signal at the sub-harmonic frequency. Continuing the above example, the second pulse may be transmitted using the entire aperture 202 or all of the n elements 104. In one embodiment, the second pulse may be transmitted at the same phase as the first pulse and in another embodiment the second pulse may be transmitted at a phase that is 180 degrees shifted from the first pulse.

At 306, the transmitter 102 transmits a third pulse at the same transmit frequency as the first and second pulses from transducer 106 and measures a third response thereto as the sub-harmonic signal at the sub-harmonic frequency. The third pulse may be transmitted using the elements 104 that were not excited in the first pulse, such as the second sub-aperture 206 or the sub-aperture 210, and the third pulse has the same phase as the first pulse transmitted using the other sub-aperture. Also, the sub-apertures used to transmit the first and third pulses combine to a total of N elements, equal to the number of elements 104 in the aperture used to transmit the second pulse. It should be understood that the first, second and third pulses may be transmitted in any order. Also, there may be more than three pulses transmitted within the pulse sequence as discussed previously.

At 308, the first, second and third responses are combined, such as by using the combining module 220, to suppress the linear echo. In some embodiments, weighting may be applied to some or all of the first, second and third responses. The weighting is used to shift the phase of either the second response or both of the first and third responses if needed. The weighting may also be referred to as a function. For example, if the first, second and third pulses correspond to [0.5, 1, 0.5] as discussed above, the weighting is [1, −1, 1], resulting in the second response being anti-symmetric with respect to the first and third responses. Alternatively, the weighting may be [−1, 1, −1]. If the pulses correspond to [0.5, −1, 0.5], the weighting is [1, 1, 1].

The responses are summed by the combining module 220 to determine a non-linear response. The linear response, representative of the tissue, will cancel out, leaving the non-linear response of the contrast agent. At 310, a representation of the non-linear response may be displayed on the display 62.

Figure 11:
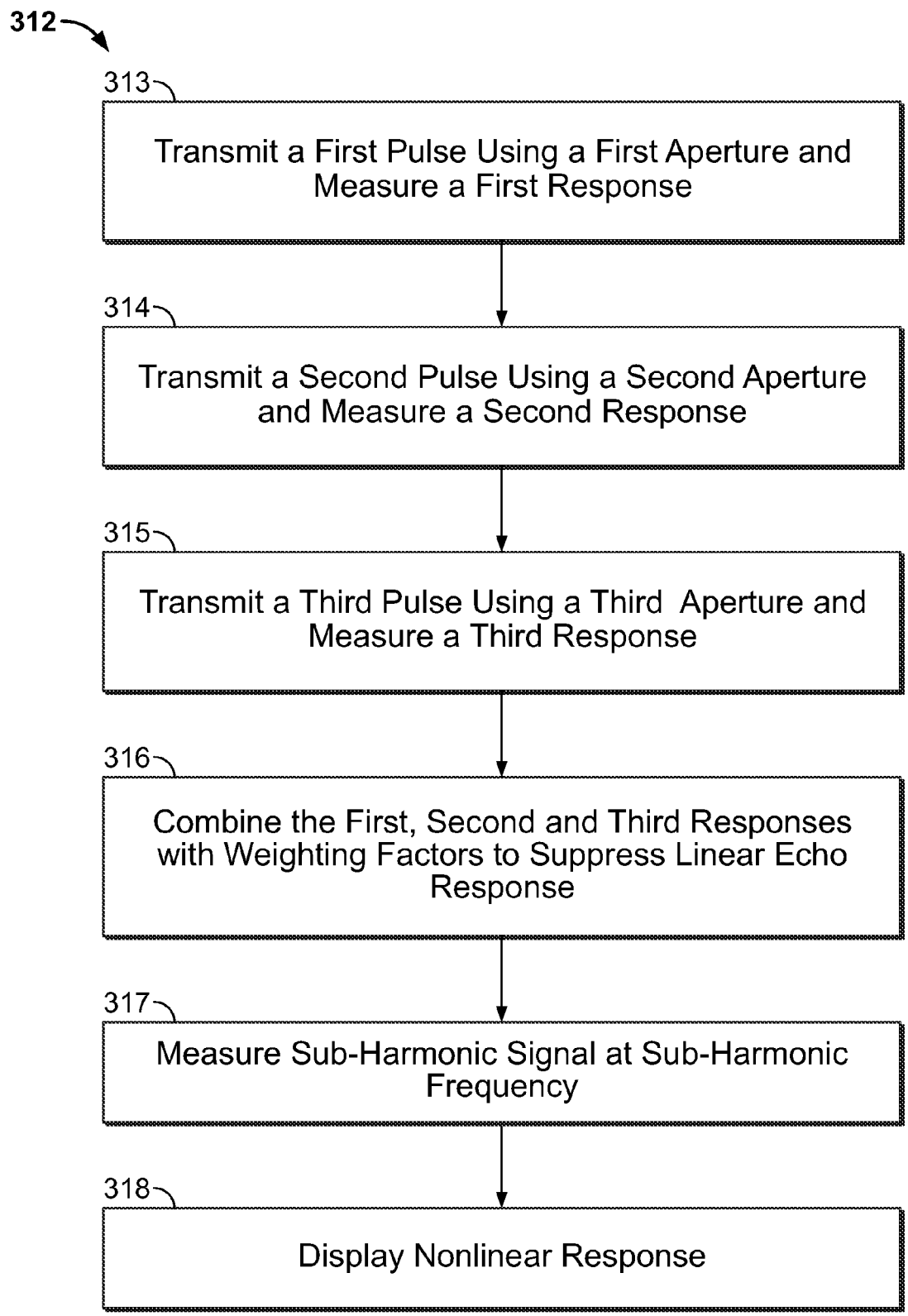

FIG. 11 illustrates another method 312 for measuring a non-linear response by detecting the sub-harmonic signal based on multiple transmit pulses with full and sub-apertures. In FIG. 10, the sub-harmonic signal was measured concurrently with or after the responses were measured or detected, and prior to combining the responses. In contrast, the method of FIG. 11 measures the sub-harmonic harmonic signal after the responses are combined. Other aspects of FIGS. 10 and 11 are the same and thus will not be described in detail.

In all transmits, each activated element 104 transmits at the same amplitude. At 313, the transmitter 102 transmits a first pulse at a transmit frequency from the transducer 106 using a portion of the aperture 202, such as the first sub-aperture 204 (of FIG. 7) or the sub-aperture 208 (of FIG. 8). The receiver 108 detects or measures a first response thereto.

At 314, the transmitter 102 transmits a second pulse at the same transmit frequency as the first pulse from transducer 106 and measures a second response thereto. The second pulse may be transmitted using the entire aperture 202 or all of the N elements 104. In one embodiment, the second pulse may be transmitted at the same phase as the first pulse and in another embodiment the second pulse may be transmitted at a phase that is 180 degrees shifted from the first pulse.

At 315, the transmitter 102 transmits a third pulse at the same transmit frequency as the first and second pulses from transducer 106 and measures a third response thereto. The third pulse may be transmitted using the elements 104 that were not excited in the first pulse, such as the second sub-aperture 206 or the sub-aperture 210, and the third pulse has the same phase as the first pulse. Again, the total number of elements 104 in the sub-apertures used to transmit the first and third pulses combine to be equal to the number of elements 104 in the aperture used to transmit the second pulse. The first, second and third pulses may be transmitted in any order, and there may be more than three pulses transmitted within the pulse sequence.

At 316, the first, second and third responses are combined to suppress the linear echo, as discussed in 308 of FIG. 10. The responses are summed by the combining module 220 to determine a non-linear response. The linear response, representative of the tissue, will cancel out, leaving the non-linear response of the contrast agent. At 317, the sub-harmonic signal is measured, such as by filtering, based on the combined signal of 316 and the transmit frequency. At 318, a representation of the non-linear response may be displayed on the display 62.

Figure 12:
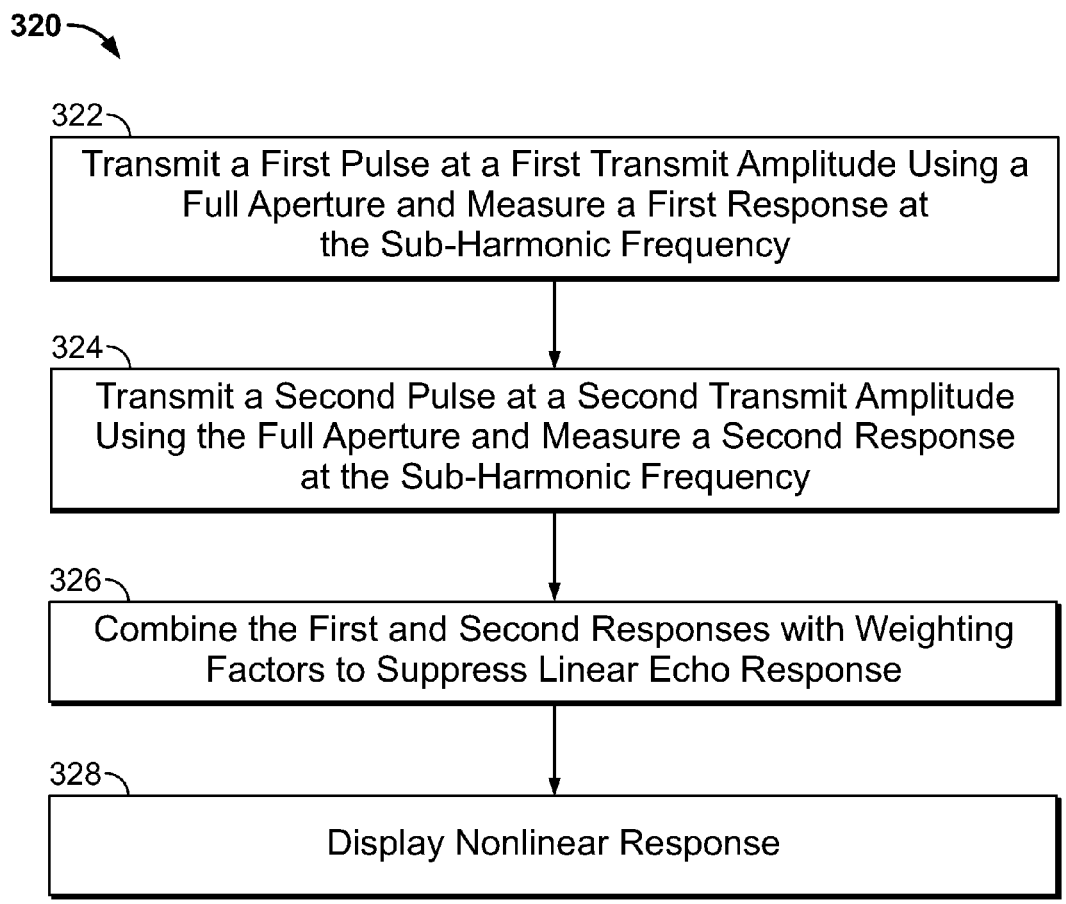
FIGS. 12 and 13 are flow charts of methods for measuring a non-linear response using transmit amplitude modulation in accordance with another embodiment of the present invention.

FIG. 12 is a method 320 that uses an imaging apparatus 50 of the type shown in FIG. 9 to transmit multiple pulses in a pulse sequence wherein the pulses have the same aperture and different transmit amplitudes and are detected at the sub-harmonic frequency. At 322, the transmitter 102 transmits a first pulse at a first amplitude and a transmit frequency from transducer 106. The first amplitude may be A1, for example. The receiver 108 measures a first response thereto at a sub-harmonic frequency that is based on the transmit frequency, as discussed above. In this example, the first pulse may be transmitted using the entire aperture 202 or the N elements 104.

At 324, the transmitter 102 transmits a second pulse from transducer 106 at a second transmit amplitude that is different than the first transmit amplitude. The second amplitude may be lesser or smaller than the first amplitude, such as 0.5*A1, but is not so limited. The same transmit frequency as the first pulse is used and a second response thereto is measured at the sub-harmonic frequency. The transmit amplitude may be varied by adjusting one or both of the transmit voltage and current. The second pulse uses the same aperture as the first pulse. Also, the first and second pulses may be transmitted in the same phase or 180 degrees different from each other.

At 326 the signal responses are combined to suppress the linear echo response. Weighting is applied to the first and second responses, such as by using combining module 220, to result in tissue signal cancellation. For example, if the first and second pulses correspond to [1, 0.5] wherein the second pulse has one-half the amplitude of the first pulse and the same phase, the weighting is [1, −2]. Alternatively, the weighting may be [−1, 2]. If the pulses correspond to [1, −0.5], the weighting is [1, 2]. Therefore, if the relative transmit amplitude and phase between the two pulses is [t1 t2], then the receiving weighting is [r1 r2] to achieve t1*r1+ t2*r2=0.

The responses are summed by the combining module 220 to determine a non-linear response. The linear response, representative of the tissue, will cancel out, leaving the non-linear response of the contrast agent. If more than 2 transmit pulses are used in the transmit sequence, the weighting factors should be selected so that t1*r1+t2*r2+t3*r3+ . . . =0. At 328, a representation of the non-linear response may be displayed on the display 62 as an ultrasound image, for example.

It should be understood that other multiplication factors may be used other than 1 and 2 to correspond to amplitudes that are different than A1 and 0.5*A1. Also, the multiplication factors may include fractional values. Also, although not discussed with reference to FIGS. 12 and 13, a transmit or receive adjustment parameter may be used to overcome non-linearity, such as within hardware components generating the transmit pulses.

Figure 13:
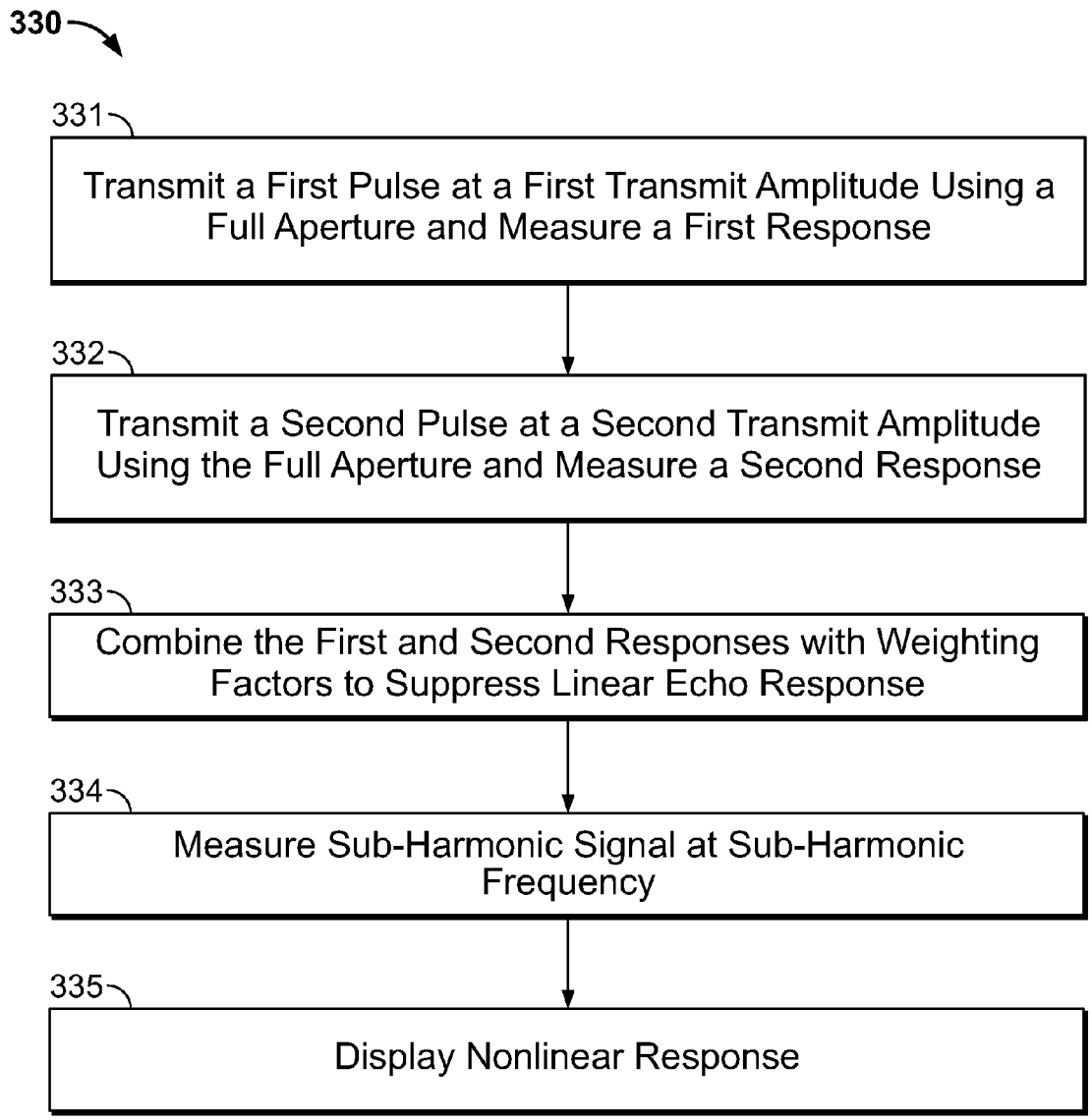

FIG. 13 is an alternative method 330 that transmits multiple pulses in a pulse sequence wherein the pulses have the same aperture and different transmit amplitudes and are detected at the sub-harmonic frequency. At 331, the transmitter 102 transmits a first pulse at a first amplitude and a transmit frequency from transducer 106, using a full aperture such as the entire aperture 202. The first amplitude may be A1, for example. The receiver 108 measures a first response thereto.

At 332, the transmitter 102 transmits a second pulse from transducer 106 at a second transmit amplitude that is different than the first transmit amplitude. The second amplitude may be lesser or smaller than the first amplitude, such as 0.5*A1, but is not so limited. The same transmit frequency and aperture as in the first pulse are used and a second response thereto is measured. The transmit amplitude may be varied by adjusting one or both of the transmit voltage and current. Also, the first and second pulses may be transmitted in the same phase or 180 degrees different from each other.

At 333 the signal responses are combined to suppress the linear echo response. Weighting is applied to the first and second responses, such as by using combining module 220, as discussed in 326 of FIG. 12. At 334, the sub-harmonic signal may be measured based on the combined signal and the transmit frequency. At 335, a representation of the non-linear response may be displayed on the display 62.

Some embodiments of the present invention provide a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for measuring a non-linear response using an imaging apparatus, said apparatus comprising at least a transmitter and a transducer comprising at least N elements that are excitable by the transmitter, wherein "N" represents a first integer number, said method comprising:
    transmitting a first pulse from the transducer at a first amplitude, a phase, and a transmit frequency and measuring a first response to the first pulse at a sub-harmonic frequency that is based on the transmit frequency, the first pulse using an aperture that comprises the N elements;
    transmitting at least second and third pulses from the transducer at second and third amplitudes, the phase, and the transmit frequency, and measuring at least second and third responses to the second and third pulses at the sub-harmonic frequency, the first, second, and third pulses transmitted at a same phase with respect to each other. the second and third pulses transmitted using first and second sub-apertures that comprise different ones of the N elements;
    combining the first, second and third responses at the sub-harmonic frequency to suppress linear echoes and to determine a non-linear response; and
    displaying a representation of the non-linear response on a display.

2. A method in accordance with claim 1, wherein the first amplitude, the second amplitude, and the third amplitude are different from one another.

3. A method in accordance with claim 1, wherein the first pulse is anti-symmetric with respect to the second and third pulses.

4. A method in accordance with claim 1, wherein the combining further comprises:
    weighting the first response or both of the second and third responses to shift the phase of the first response or the phases of the second and third responses by 180 degrees; and
    adding the first, second and third responses.

5. A method in accordance with claim 1, further comprising shifting the phase of the first pulse 180 degrees from the phase of the second and third pulses, the combining further comprising adding the first, second and third responses.

6. A method in accordance with claim 1, wherein the first and second sub-apertures each comprise one-half of the N elements on opposite sides of the transducer.

7. A method in accordance with claim 1, wherein the first and second sub-apertures comprise one of interleaved halves of the N elements, random halves of the N elements, patterned halves of the N elements, pseudo-random halves of the N elements, or periodic halves of the N elements.

8. A method in accordance with claim 1, further comprising transmitting a sequence of pulses from the transducer and measuring associated responses at the sub-harmonic frequency, wherein each of the pulses in the sequence is transmitted using a different subset of the elements in the transducer and a sum of a number of the elements in all of the subsets is equal to N.

9. A method in accordance with claim 1, wherein the sub-harmonic frequency is less than the transmit frequency.

10. A method in accordance with claim 1, further comprising weighting one or more of the first response, the second response, or the third response by at least one receive weighting such that a sum of products of an amplitude and the receive weighting for each of the one or more of the first response, the second response, or the third response is zero.

11. A method in accordance with claim 1, wherein a sum of the elements of the transducer within the first and second sub-apertures is equal to N.

12. A diagnostic imaging apparatus for measuring a non-linear response comprising:
    a transducer having at least N elements excitable by the transmitter, wherein "N" represents an integer number, the transducer configured to transmit a first pulse at a first amplitude, a phase, and a transmit frequency using an aperture that comprises the N elements, the transducer also configured to transmit at least a second pulse and a third pulse at second and third amplitudes, the phase, and the transmit frequency, the second pulse transmitted using a first sub-aperture formed by a first subset of the N elements, the third pulse transmitted using a second sub-aperture formed by a different, second subset of the N elements;
    a receiver configured to receive echo return signals from the elements and determine a first response to the first pulse, a second response to the second pulse, and a third response to the third pulse at a sub-harmonic frequency;
    a combining module configured to combine the first response, the second response, and the third response as a combined response, the combining module configured to measure a sub-harmonic signal based on the combined response at a sub-harmonic frequency to suppress linear echoes and determine a non-linear response; and
    a display configured to display a representation of the determined non-linear response.

13. An apparatus in accordance with claim 12, wherein the transducer is configured to shift the phase of the first pulse 180 degrees from the phase of the second and third pulses.

14. An apparatus in accordance with claim 12, wherein the sub-harmonic frequency is less than the transmit frequency.

15. An apparatus in accordance with claim 12, wherein the combining module is configured to weigh one or more of the first response, the second response, or the third response by at least one receive weighting such that a sum of products of an amplitude and the receive weighting for each of the one or more of the first response, the second response, or the third response is zero.

16. A method for measuring a non-linear response to ultrasound pulses using an ultrasound imaging apparatus, said method comprising:
    transmitting a first pulse from a transducer at a first transmit amplitude, a phase, and a transmit frequency, the first pulse transmitted using N elements of the transducer, wherein N represents a first integer number;
    measuring a first response to the first pulse;
    transmitting a second pulse from the transducer using the N transducer elements at a second transmit amplitude that is reduced relative to the first transmit amplitude. the phase, and the transmit frequency;

measuring a second response to the second pulse, wherein at least one of the first response or the second response is measured at a sub-harmonic frequency that is based on the transmit frequency;

combining the first and second responses to suppress linear echoes and determine a non-linear response; and displaying a representation of the non-linear response on the display.

17. The method of claim 16, wherein at least one of measuring the first response or measuring the second response occurs prior to combining the first and second responses.

18. The method of claim 16, wherein combining the first and second responses includes multiplying the second response by a multiplier based on the first transmit amplitude and the second transmit amplitude and multiplying one of the first and second responses by −1.

19. The method of claim 16, further comprising shifting the phases of the first and second pulses 180 degrees with respect to each other, and wherein combining the first and second responses includes multiplying the second response by a multiplier such that the first response and the second response have a same amplitude.

20. The method of claim 16, further comprising:

transmitting a plurality of the pulses that include at least the first pulse, the second pulse, and the third pulse;

measuring associated responses of the pulses, the associated responses including at least the first response, the second response, and the third response; and weighting the associated responses by one or more receive weighting values so that a sum of products of an amplitude and the receive weighting value for each of the pulses and the associated response is zero.

21. The method of claim 16, further comprising transmitting a sequence of pulses from the transducer and measuring associated responses at the sub-harmonic frequency, wherein each of the pulses in the sequence is transmitted using a different subset of the elements in the transducer and a sum of a number of the elements in all of the subsets is equal to N.

22. The method of claim 16, wherein the sub-harmonic frequency is less than the transmit frequency.

\* \* \* \* \*